United States Patent [19]

Kerwin et al.

[11] Patent Number: 5,929,031
[45] Date of Patent: *Jul. 27, 1999

[54] STORAGE STABLE HEMOGLOBIN SOLUTIONS

[75] Inventors: Bruce A. Kerwin; Douglas L. Looker, both of Lafayette, Colo.

[73] Assignee: Baxter Biotech Technology Sàrl, Neuchâtel, Switzerland

[ * ] Notice: This patent issued on a continued prosecution application filed under 37 CFR 1.53(d), and is subject to the twenty year patent term provisions of 35 U.S.C. 154(a)(2).

[21] Appl. No.: 08/433,896

[22] Filed: May 2, 1995

[51] Int. Cl.$^6$ .......................... A61K 38/16; A61K 35/14; C07K 1/00
[52] U.S. Cl. .................................. 514/12; 514/6; 530/385
[58] Field of Search ........................... 514/6, 12; 530/385

[56] References Cited

U.S. PATENT DOCUMENTS

| | | | |
|---|---|---|---|
| 4,727,027 | 2/1988 | Wiesehahn et al. | 435/173 |
| 4,777,244 | 10/1988 | Bonhard et al. | 530/385 |
| 4,861,867 | 8/1989 | Estep | 530/385 |
| 5,234,903 | 8/1993 | Nho et al. | 514/6 |
| 5,352,773 | 10/1994 | Kandler et al. | 530/385 |

FOREIGN PATENT DOCUMENTS

| | | |
|---|---|---|
| 9202239 | 2/1992 | WIPO . |
| 9208478 | 5/1992 | WIPO . |
| 9426286 | 11/1994 | WIPO . |

OTHER PUBLICATIONS

Akers, M.J., Antioxidants in pharmaceutical products, J. of Parenteral Science and Tech., 36(5), pp. 222–228, 1982.
Stratton et al., The reduction of methemoglobin levels by antioxidants, Hemoglobin, 12(4), pp. 353–368, 1988.
Kothe et al., Characterization of a Modified, Stroma–Free, Hemoglovin Solution as an Oxygen–Cattying Plasma Substitute, Surgery, GYN. & OB., 161, pp. 563–569, 1985.
Akers, M.J./Antioxidants in Pharmaceutical Products/J. of Parenteral Science & Tech./ (1982) 36(5): 222–228.
Antonini, E./ The Derivatives of Ferrous Hemoglobin and Myoglobin/Hemoglobin & Myoglobin in Their Reactions With Ligands/(1971) 21: 13–39/Chapter 2/North–Holland Research Monographs/Eds. Antonini & Brunori.
Christensen, S.M. et al/Preparation of Human Hemoglobin Ao for Possible Use as a Blood Substitute/J. of Biochemical & Biophysical Methods/(1988) 17: 143–154.
Clerc, Y et al/ Préparation et Conservation De Solutions D'Hémoglobine Modifiée/Travaux Scientifiques Des Chercheurs Du Service De Santé Des Armées/(1987) 8: 211.
Devenuto, F./Stability of Hemoglobin Solution During Extended Storage/J. Lab. Clin. Med./(1978) 92(6): 946–952.
Di Iorio, E.E./Preparation of Derivatives of Ferrous and Ferric Hemoglobin/Methods in Enzymology/(1981) 76: 57–72.
Eyer, P. et al/Kinetics of Ferrihemoglobin Formation by Some Reducing Agents, and the Role of Hydrogen Peroxide/Molecular Pharmacology/(1975) 11: 326–334.
Gibson, Q.H./The Reduciton of Methaemoglobin by Ascorbic Acid/Biochemical Journal/(1943) 37: 615–618.
Keipert, P.E. et al/Pyridoxylated–Polyhemoglobin Solution: A Low Viscosity Oxygen–Dellivering Blood Replacement Fluid with Normal Oncotic Pressure and Long–Term Storage Feasibility/Biomat., Art. Cells, Art. Org.,/(1988) 16(1–3): 185–196.
Kikugawa, K. et al/Factors Influencing the Autoxidatin of Hemoglobin A/Chem. Pahrm. Bull./(1981) 29: 1382–1389.
Kothe, N. et al/Characterization of a Modified, Stroma–Free Hemoglobin Solution as an Oxygen–Carrying Plasma Substitute/Surgery, Gyn. & Ob./(1985) 161: 563–569.
Kramlova, M. et al/Stroma–Free Haemoglobin Solution for Infusion: Changes During Storage/Haematologia/ (1976) 10(3–4): 365–371.
Moore, G.L. et al/Evaluation of Methemoglobin Formation During the Storage of Various Hemoglobin Solutions/Artif Organs/(1992) 16(5): 513–518.
Stratton, L.P. et al/The Reduction of Methemoglobin Levels by Antioxidants/Hemoglobin/(1988) 12(4):353–368.

*Primary Examiner*—Cecilia J. Tsang
*Assistant Examiner*—Anish Gupta
*Attorney, Agent, or Firm*—Senniger, Powers, Leaviatt & Roedel

[57] ABSTRACT

The present invention relates to storage stable hemoglobin solutions which contain partially deoxygenated and surprisingly low amounts of reducing agents. Methods for preparing such storage stable hemoglobin solutions are also provided as well as a systems for storing the solutions.

30 Claims, 1 Drawing Sheet

FIGURE 1

STORAGE STABLE HEMOGLOBIN SOLUTIONS

FIELD OF INVENTION

The present invention relates to storage stable hemoglobin solutions, and more particularly to solutions containing partially deoxygenated hemoglobin and reducing agents.

BACKGROUND OF THE INVENTION

The oxygen carrying portion of the red blood cell is hemoglobin, a tetrameric protein molecule composed of two identical alpha globins ($\alpha_1$, $\alpha_2$), two identical beta globins ($\beta_1$, $\beta_2$) and four heme molecules. A heme molecule is incorporated into each of the alpha and beta globins to give alpha and beta subunits. Heme is a macrocyclic organic molecule that contains an iron atom at its center; each heme can combine reversibly with one ligand molecule, for example oxygen. In a hemoglobin tetramer, each alpha subunit is associated with a beta subunit to form two stable alpha/beta dimers, which in turn associate to form the tetramer (a homodimer). The subunits are noncovalently associated through Van der Waals forces, hydrogen bonds and salt bridges.

In the unliganded state (deoxygenated or "deoxy") state, the four subunits form a quaternary structure known as "T" (for "tense") state. During ligand binding, the $\alpha_1\beta_1$ and $\alpha_2\beta_2$ interfaces remain relatively fixed while the $\alpha_1\beta_2$ and $\alpha_2\beta_1$ interfaces exhibit considerable movement. When a ligand is bound to the hemoglobin molecule, the globins move with respect to each other, and as a result intersubunit distances are increased relative to the deoxygenated distances. Thus, when a ligand is bound at the heme groups, the molecule assumes the "relaxed" or "R" quaternary structure, the thermodynamically stable form of the molecule when ligands are bound at three or more hemes.

Ligands, particularly oxygen, bind reversibly to the reduced form of the iron (ferrous, $Fe^{+2}$) in the heme. When the iron in the heme is oxidized to $Fe^{+3}$ (the ferric form of iron), oxygen and some other ligands cannot bind to the iron of the heme and the hemoglobin is non-functional in terms of oxygen transport. The iron in the heme groups may be oxidized in a number of fashions. For example, the iron may oxidize through a pathway mediated by binding of a water molecule at the heme iron to produce methemoglobin ("autoxidation"). Autoxidation can be enhanced by the presence of trace metals in solution. Methemoglobin can also be produced as a result of direct oxidation by chemicals with higher redox potentials, such as ferricyanide, or by indirect oxidation by reducing agents through a hydrogen peroxide mediated pathway (Castro, C. E. et al., in: *Biochemical and Clinical Aspects of Hemoglobin Abnormalities*, Academic Press, Inc., pp 495–503, 1978). Furthermore, deoxyhemoglobin can be oxidized to methemoglobin by chemicals such as ferricyanide even in the absence of oxygen. The protein itself may be oxidized as well, without concommittant oxidation of the iron in the heme groups. For example, hemoglobin may be oxidatively denatured by chemicals such as hydrazine without going through a methemoglobin intermediate. (see Bunn, H. F. and Forget, B. G. *Hemoglobin: Molecular, Genetic and Clinical Aspects*, W.B. Saunders Company, Philadelphia, pp 634–662 for review).

However produced, methemoglobin is a non-functional form of hemoglobin that cannot bind oxygen or carbon monoxide and shows significantly altered nitric oxide binding characteristics. Methemoglobin molecules are vulnerable to accelerated degradation due to hemichrome formation, heme loss, precipitation, reaction with hydrogen peroxide to form toxic radicals and the like.

In addition to the reduction of functionality of a hemoglobin solution by the formation of methemoglobin, the protein portions of the hemoglobin molecule can be modified and altered by oxidative damage. For example, the oxidation of the iron of the heme results in the production of hydrogen peroxide (Watkins, J. A. *Bioc. Biophys. Res. Comm.* 132: 742–748, 1985) as well as superoxide (Thillet, J. and Michelson, A. M., *Free Rad. Res. Comm.* 1: 89–100, 1985). These activated oxygen species can then damage the hemoglobin protein, for example, by causing polymerization of the molecule (Thillet, J., supra) or by damaging individual amino acids and thereby disrupting tertiary structure (Stefek, R. P. and Thomas, M. J., *Free Rad. Res. Comms.* 12–13: 489–497, 1991). These changes can result in increased immunogenicity (Riechlin, M., *Adv. Immunol.* 20: 71–132, 1975; Noble, R. W. et al. *Bioc.* 11: 3326–3332, 1972). Ultimately, damage resulting from activated oxygen species, irrespective of source, may lead to oxidative denaturation of the molecule and its precipitation. Therefore, during storage of hemoglobin solutions, the avoidance of oxidation, whether of the protein itself or of the heme groups within the protein, is necessary to maintain functionality and the tertiary and quaternary structure of hemoglobin in solution and to limit immunogenicity.

It has long been known that hemoglobin solutions form methemoglobin more slowly if stored under deoxygenated conditions rather than oxygenated conditions (Antonini and Brunori, *Hemoglobin and Myoglobin in Their Reactions with Ligands*, North Holland Publishing Company, Amsterdam 13–39, 1971; Di Iorio, E. E., *Meth. Enzymol.* 76: 57–72, 1981). However, preservation of hemoglobin under deoxygenated conditions poses significant technical difficulties (Di Iorio, E. E., *Meth. Enzymol.* 76: 57–72, 1981), or requires the addition of potentially toxic chemicals. Moreover, the choice of exogenous chemical agents has been extremely difficult since these additives can act as oxidants or reductants, depending on the conditions of the solution and unpredictable protein/agent interactions (Akers, M. J. *J. Parent. Sci. Tech.* 36: 222–228, 1982). In the case of hemoglobin solutions, the choice of an exogenous chemical agent that will act as a reductant is further complicated by the fact that not all reducing agents can reduce hemoglobin, and some reducing agents may act as oxidants in a given hemoglobin formulation (Eyer, P., *Mol. Pharmacol.* 11: 326–334, 1975; Kikugawa, K. *Chem. Pharm. Bulletin* 29: 1382–1389, 1981; Stratton, L. P. *Hemoglobin* 12: 353–368, 1988). If the exogenous chemical does act to reduce methemoglobin formation in solution, there may be unexpected side reactions that can affect the protein structure (Antonini and Brunori, *Hemoglobin and Myoglobin in Their Reactions with Ligands*, North Holland Publishing Company, Amsterdam 13–39,1971).

In order to reduce or eliminate the need for exogenous reducing agents during storage, Nho (PCT publication WO 92/08478) designed an apparatus which allowed the rapid deoxygenation of hemoglobin solutions. Hemoglobin solutions were deoxygenated by passing the solution through one side of a gas exchange device and passing an inert gas, nitrogen, on the other side of a gas permeable membrane. The hemoglobin was circulated until it was at least 90% deoxygenated. No exogenous reductants were added to the hemoglobin solution; oxidation, although not completely eliminated, was slowed by careful removal of oxygen in the hemoglobin solution. Thus there was no introduction of chemical reductants which might elicit unforeseen biological responses when used in pharmaceutical formulations, or which might react with the hemoglobin itself in an unpredictable fashion.

A different approach to the storage of hemoglobin solutions was described by Kandler, R. L. and J. C. Spicuzza (U.S. Pat. No. 5,352,773 and PCT publication WO 92/02239). They utilized the intrinsic ability of a purified di-aspirin crosslinked hemoglobin solution to "auto-reduce" in the absence of any exogenous chemical reductants. In their solutions, methemoglobin concentrations were reduced by storing the solutions in overwrapped, oxygen impermeable containers. Some of these overwrapped containers contained oxygen scavenging pouches placed between the overwrap and the inner container. Methemoglobin concentrations as high as 50% could be reduced to levels as low as 1.5% by storage alone as long as oxygen was rigorously excluded from the containers during the storage of the solution. This methodology did not depend on whether or not the initial solution was deoxygenated prior to storage. However, even though this methodology did not require the addition of exogenous reducing agents, the material was held for long periods of time to ensure methemoglobin was reduced to clinically acceptable levels, and/or it was held at relatively high temperatures. Extended storage or storage at elevated temperatures might result in modifications of the hemoglobin structure or growth of microorganisms if inadequately sterilized.

Deoxygenation of hemoglobin solutions alone may not provide sufficient stability to the hemoglobin solutions to allow for long term storage, especially storage at room temperature. For example, DeVenuto (DeVenuto, F., *J. Lab. Clin. Med.* 92: 946–952, 1978) found that deoxygenated hemoglobin solutions showed more rapid methemoglobin formation than comparable solutions stored in the presence of oxygen. Moreover, he was not able to demonstrate any solution that showed stability at room temperature.

Ascorbate (ascorbic acid or vitamin C) has been commonly used both in pharmaceutical compositions and as a reagent to scavenge oxygen or act as an antioxidant in hemoglobin compositions. As a pharmaceutical, ascorbate has been administered directly to treat methemoglobinemia in vivo (Kiese, M. *Methemoglobinemia: A Comprehensive Treatise*, CRC Press, Inc., Cleveland, Ohio, pg. 23, 1974; Deeny, J., et al., *Br. Med. J.* 1: 721–723, 1943). Ascorbate has been used as a preservative and a stabilizer in many protein solutions, particularly proteins derived from blood products. For example, G. P. Wiesehahn et al. (U.S. Pat. No. 4,727,027) described the decontamination of solutions of biologically active proteins derived from blood or blood components, particularly Factor VIII, by photodecontamination. They stabilized solutions of Factor VIII prior to photodecontamination by deoxygenating the solutions either by the addition of high concentrations of oxygen scavengers, such as 10 mM ascorbate, by flushing with inert gases, or both addition of oxygen scavengers and flushing with inert gas. Österber et al. (PCT publication WO 94/26286) also describe a stabilized, deoxygenated formulation of factor VIII augmented with antioxidants such as glutathione, acetylcysteine, methionine, tocopherol, butyl hydroxy toluene, butyl hydroxy anisole or phenolic compounds. Although these antioxidants are suitable for use at low doses and are thus appropriate for the small dosage volumes of Factor VIII, many of these antioxidants can be toxic at high doses and hence are not appropriate for use in formulations where high volumes of a therapeutic, for example, hemoglobin, might be administered. In addition, the application is silent with respect to the interaction of the antioxidants and hemoglobin. It is of note that Österber et al. report that the addition of ascorbate to a deoxygenated solution of Factor VIII resulted in reduced Factor VIII stability.

As early as the 1940's, high concentrations of ascorbate were used to reduce methemoglobin in hemoglobin compositions (Gibson, Q. H., *Bioc. I.* 37: 615–618, 1943). However, the interaction of ascorbate and hemoglobin have been unpredictable. For example, Kikugawa et al. (Kikugawa, K. et al., *Chem. Pharm. Bull.* 29: 1382–1389, 1981) noted that ascorbate acted as a prooxidant, in fact enhancing oxidation, when added to oxygenated formulations of hemoglobin. Kramlová et al. (Kramlová, M. et al., *Haematologia* 10: 365–371, 1976 ) and Stratton et al., supra, suggested that addition of ascorbate to hemoglobin solutions also resulted in enhanced oxidation rather than protection from oxidation.

Ascorbate at relatively high concentrations has been used with some success to stabilize deoxygenated hemoglobin solutions. For example Bonhard et al. (U.S. Pat. No. 4,777,244) used ascorbate as an oxygen scavenger in a hemoglobin solution prior to crosslinking deoxygenated hemoglobin. They emphasized the need to use high levels of ascorbate (at least 4 moles of ascorbic acid per mole of hemoglobin) to ensure that all oxygen was scavenged in the hemoglobin solution. Kothe et al. (Kothe, N., Eichentopf, B. and Bonhard, K. *Surg. Gyn. Obst.* 161: 563–569 1985) also used ascorbate to stabilize a deoxygenated hemoglobin solution. These authors used 5.45 mM ascorbate in a 8.5 gm/dl hemoglobin solution (~4 moles ascorbate per mole of hemoglobin) and reported no significant formation of methemoglobin in the hemoglobin formulation after storage at 4° C. for one year. Clerc et al. (Clerc, Y. et al., *Service de Santé des Armées Trav. Scient.* 8: 211, 1987) reported similar low levels of methemoglobin formation in a formulation based on the Kothe solution (4:1 molar ratio ascorbate to hemoglobin) during storage for 11 months at 4° C. Kikugawa et al., supra, reported that dilute (250 mg/dl) deoxygenated hemoglobin solutions treated with 5 mM ascorbate (~13:1 molar ratio ascorbate to hemoglobin) were stable for the 60 minutes of their study. Long term stability of deoxygenated ascorbate containing solutions was not discussed by these authors. Nho et al. (U.S. Pat. No. 5,234,903) followed methemoglobin formation in a 5–6 gm/dl deoxygenated bovine hemoglobin solution and found that 30 mM cysteine was 5 times more effective for the prevention of methemoglobin formation than the same amount of ascorbate (~35:1 molar ratio ascorbate:hemoglobin). Moreover, the addition of ascorbate to their hemoglobin formulation resulted in significant release of free iron. Indeed, Estep discussed the requirement that reductants that are added to hemoglobin solutions must have redox potentials higher than ascorbate to maintain these solutions under deoxygenated conditions; ascorbate is simply not sufficiently reducing to maintain the deoxygenation of hemoglobin solutions (Estep, T. N. U.S. Pat. No. , 4,861,867). Note that all compositions that have used ascorbate as an antioxidant or an oxygen scavenger have used at least a 4:1 molar ratio of ascorbate to hemoglobin.

Storage of previously known hemoglobin formulations at room temperature has proven problematic (Keipert, P. E. and Chang, T. M. S., *Biomat., Art. Cells, Art. Org.*, 16: 185–196, 1988; Christensen, S. M. et al., *J. Bioc. Biophys. Meth.* 17: 143–154, 1988; Moore, G. L. et al., *Artif. Organs* 16: 513–518, 1992). Recently, however, Kandler and Spicussa (PCT publication WO 92/02239) and Nho (PCT publication WO 92/08478) have been able to demonstrate slow or no methemoglobin formation in hemoglobin solutions stored under deoxygenated conditions without addition of exogenous chemical reductants at room temperature for periods of up to 10 months.

The present invention is based on the surprising finding that hemoglobin undergoes significant modifications that may have physiological implications even prior to the appearance of significant quantities of methemoglobin. Furthermore, it has been discovered that there is a relationship between the amount of oxygen in a hemoglobin formulation and the amount of ascorbate required to stabilize the hemoglobin. In addition, it has been surprisingly discovered that certain ratios of hemoglobin, reducing agent and oxygen improve the stability of hemoglobin during storage.

SUMMARY OF THE INVENTION

The present invention relates to storage stable hemoglobin compositions comprising partially deoxygenated hemoglobin solutions and less than 4 moles of reducing agent per mole of hemoglobin, preferably less than three moles of reducing agent per mole of hemoglobin, and more preferably less than two moles of reducing agent per mole of hemoglobin. The reducing agent is selected from the group consisting of dithionite, sodium borohydride and ascorbate, and is most preferably ascorbate. The partially deoxygenated hemoglobin solution contains less than 5000 parts per million of oxygen, more preferably less than 500 parts per million of oxygen, most preferably less than 150 parts per million.

The storage stable hemoglobin composition of the instant invention is storage stable for at least three months, more preferably for at least six months, most preferably for at least one year. The compositions of the present invention can be stored at temperatures less than about 40° C., more preferably at less than about 25° C. or about 4° C. or less, depending on the intended use and the desired storage conditions. In addition, the present invention provides formulations comprising partially deoxygenated hemoglobin, less than 4 moles of reducing agent per mole of hemoglobin, pharmaceutically acceptable carriers and chelating agents at pH between about 6.5 and 9.5, preferably pH 6.6 to 7.8, most preferably pH 6.8 to 7.6. Preferably the chelating agent is EDTA or DTPA, more preferably the chelating agent is EDTA.

The present invention provides methods for the preparation of the storage stable hemoglobin composition of the invention comprising combining a reducing agent with partially deoxygenated hemoglobin solutions at ratios less than 4 moles of reducing agent per mole of hemoglobin. Methods for partial deoxygenation of a hemoglobin solution include gas-liquid contacting methods.

Additionally, the present invention provides systems for storage of hemoglobin solutions. The systems include the storage stable hemoglobin compositions of the present invention in suitable containers.

DETAILED DESCRIPTION OF THE INVENTION

Figure 1:
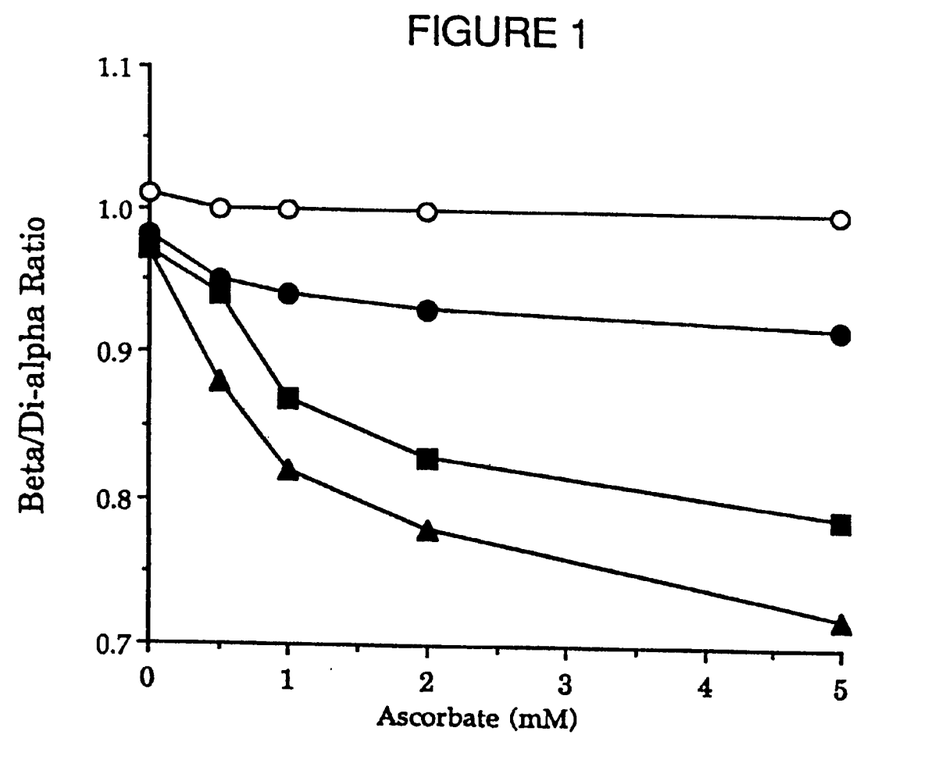
FIG. 1 is a graph of the beta/di-alpha ratio on the y axis and the ascorbate concentration in mM on the x axis. The beta/di-alpha ratios were determined from reverse phase HPLC chromatograms. Samples were analyzed at 21 days after storage with 150 ppm oxygen (-○-), 1000 ppm oxygen (-●-), 5000 ppm oxygen (-■-) and 15000 ppm oxygen (-▲-). Lower values for the beta/di-alpha ratio indicate a greater amount of modified beta globin.

The present invention relates to storage stable hemoglobin solutions that are partially deoxygenated and contain less than 4 moles of reducing agent per mole of hemoglobin and methods of making such storage stable hemoglobin solutions.

Hemoglobin can be free in solution, or in solution in a naturally occurring or artificial cell (e.g. liposomes) and can be derived from natural, synthetic or recombinant sources. For example, slaughter houses produce very large quantities of hemoglobin-containing blood. Particular species or breeds of animals which produce a hemoglobin especially suitable for a particular use can be specifically bred in order to supply hemoglobin. Transgenic animals can be produced that express non-endogenous hemoglobin (Logan, J. S. et al., PCT application PCT/US92/05000). Human hemoglobin can be collected from outdated human blood that must be discarded after a certain expiration date.

In addition to extraction from animal sources, the genes encoding subunits of a desired naturally occurring or mutant hemoglobin can be cloned, placed in a suitable expression vector and inserted into an organism, such as a microorganism, animal or plant, or into cultured animal or plant cells or tissues. These organisms can be produced using standard recombinant DNA techniques and the hemoglobin produced by these organisms can then be expressed and collected as described, for example, in Hoffman, S. J. and Nagai, K. in U.S. Pat. No. 5,028,588 and Hoffman, et al., WO 90/13645, both herein incorporated by reference.

Purification of hemoglobin from any source can be accomplished using purification techniques which are known in the art. For example, hemoglobin can be isolated and purified from outdated human red blood cells by hemolysis of erythrocytes followed by chromatography (Bonhard, K., et al., U.S. Pat. No. 4,439,357; Tayot, J. L. et al., EP Publication 0 132 178; Hsia, J. C., EP Patent 0 231 236 B1), filtration (Rabiner, S. F. (1967) et al., J. Exp. Med. 126: 1127–1142; Kothe, N. and Eichentopf, B. U.S. Pat. No. 4,562,715), heating (Estep, T. N., PCT publication PCT/US89/014890, Estep, T. N., U.S. Pat. No. 4,861,867), precipitation (Simmonds, R. S. and Owen, W. P., U.S. Pat. No. 4,401,652; Tye, R. W., U.S. Pat. No. 4,473,494) or combinations of these techniques (Rausch, C. W. and Feola, M., EP 0 277 289 B1). Recombinant hemoglobins produced in transgenic animals have been purified by chromatofocusing (Townes, T. M. and McCune, PCT publication PCT/US/09624) while those produced in yeast and bacteria have been purified by ion exchange chromatography (Hoffman, S. J. and Nagai, K. in U.S. Pat. No. 5,028,588 and Hoffman, et al., WO 90/13645).

The hemoglobin may be modified by genetic or chemical means for particular uses either prior to, during or after purification. For example, the oxygen affinity may be altered by chemical modification or by genetic modification of the hemoglobin through the introduction of appropriate mutations. The hemoglobin may be chemically crosslinked, or genetically linked or both chemically crosslinked and genetically linked to prevent the dissociation of the molecule into alpha/beta subunits (dimerization), prevent heme loss, or to increase the size of the molecule.

Hemoglobin solutions can be partially deoxygenated by any means known in the art. Treatment of hemoglobin solutions with an inert gas such as nitrogen or argon is one such approach. This can be accomplished using gas-liquid contacting techniques wherein oxygen is transported from a solution to a non-oxygen gas phase. Some options for gas-liquid contacting include: packed columns, in which the non-oxygen gas passes upward while a solution trickles downward through a bed of packing; plate columns, similar to packed columns except that they contain a series of horizontal plates that catch the solution; wetted-wall columns in which a solution falls as a film down a bank of vertical tubes; gas transfer membranes, wherein oxygen is transported across a thin membrane that retains liquid on one side and a non-oxygen gas on the other side; gas-sparged tanks, in which non-oxygen gas bubbles through a tank containing the solution; cyclic pressurization, in which a vessel containing the solution is cyclically pressurized with a non-oxygen gas then vented to release the gas and induce bubbles to form in the solution; and liquid atomization, in which the solution is sprayed into a chamber containing a non-oxygen gas.

Another approach to deoxygenation is liquid-liquid contacting techniques, in which two immiscible liquids are mixed together, one of which contains no dissolved oxygen but in which oxygen readily dissolves. After the second liquid has absorbed the oxygen, the liquids can be separated by gravity or in a centrifuge.

A third approach to deoxygenation is sorption, in which solid particles with a large internal surface area that adsorb dissolved oxygen, for example molecular sieves, are added to a solution. After sorption, the solid particles can be separated from the solution with a centrifuge or filter.

Of these techniques, a particularly useful technique is the use of a packed column, where the solution is deoxygenated by flowing an oxygenated hemoglobin solution over the column, while flowing an inert gas countercurrent to the flow of the hemoglobin solution. The inert gas is any gas that does not bind at the heme group of a hemoglobin molecule, for example argon or nitrogen. In another embodiment, the solution is deoxygenated by repeatedly evacuating a hemoglobin solution and flushing or sweeping the hemoglobin formulation with an inert gas, such as argon or nitrogen, until the desired residual oxygen concentration is obtained to produce a partially deoxygenated hemoglobin solution.

A partially deoxygenated hemoglobin solution is a hemoglobin solution that contains less than about 5,000 parts per million by volume (ppm) oxygen in the headspace. Residual oxygen in the hemoglobin solution is preferably less than about 1000 ppm, more preferably less than about 500 ppm, and still more preferably less than about 150 ppm. Residual oxygen in the headspace can be measured by any means known in the art including for example, sampling of the headspace and measurement of the oxygen in the headspace using a suitably equipped gas chromatograph or zirconium-based detector. For example, the residual oxygen concentration can be determined by sampling of the fill environment using a "MOCON" (Mocon, Minneapolis, Minn.) analyzer.

The fill environment is the environment in which the hemoglobin is prepared for storage as described, for example, in Example 2. Fill environments include but are not limited to glove bags, glove boxes or any suitable environment in which the residual oxygen levels are controlled. The headspace above the hemoglobin formulation is considered to be in equilibrium with the fill environment. If there is no headspace in the container, then the solution is considered to be in equilibrium directly with the fill environment. If the solution is placed into a container that has been evacuated prior to filling, then the hemoglobin is considered to be in equilibrium with the last gas with which it was in contact.

In addition to partially deoxygenated hemoglobin, the solutions of the instant invention also contain reducing agents. Such reducing agents include but are not limited to dithionite, ferrous salts (for example ferrous pyrophosphate), sodium borohydride as well as other borohydrides, alpha tocopherol and ascorbate or salts therof. If the hemoglobin solution of the instant invention as a pharmaceutical, then the reducing agent is preferably a pharmaceutically acceptable reducing agent. If the hemoglobin solution of the present invention is to be used in a non-pharmaceutical application, then the reducing agent can be any reducing agent, whether or not pharmaceutically acceptable. Preferably, the reducing agent is sodium ascorbate.

The reducing agent can be added before or after partial deoxygenation. Preferably, the reducing agent is added after the target residual oxygen level is achieved in the hemoglobin formulation. Although the reducing agent can be in a liquid or solid form, the reducing agent is especially useful when it is in a thoroughly deoxygenated concentrated liquid solution. The amount of the reducing agent in the composition of the instant invention is less than 4 moles/mole of hemoglobin, more preferably less than 2 moles of reducing agent/mole of hemoglobin.

The formulations can include other components in addition to the partially deoxygenated hemoglobin solution and one or more reducing agents. The hemoglobin solution of the invention can be formulated in any composition suitable for pharmaceutical or non-pharmaceutical uses. For example, a parenteral therapeutic composition can comprise a sterile isotonic saline solution containing between 0.001% and 90% (w/v) hemoglobin. Suitable compositions can also include 0–200 M of one or more buffers (for example, acetate, phosphate, citrate, bicarbonate, or Good's buffers). Salts such as sodium chloride, potassium chloride, sodium acetate, calcium chloride, magnesium chloride can also be included in the compositions of the invention at concentrations of 0–2 M. In addition, the compositions of the invention can include 0–2 M of one or more carbohydrates (for example, reducing carbohydrates such as glucose, maltose, lactose or non-reducing carbohydrates such as sucrose, trehalose, raffinose, mannitol, isosucrose or stachyose) and 0–2 M of one or more alcohols or poly alcohols (such as polyethylene glycols, propylene glycols, dextrans, or polyols). The compositions of the invention can also contain 0.005–1% of one or more surfactants and 0–200 $\mu$M of one or more chelating agents (for example, ethylenediamine tetraacetic acid (EDTA), ethylene glycol-bis ($\beta$-aminoethyl ether) N,N,N',N'-tetraacetic acid (EGTA), ophenanthroline, diethylamine triamine pentaacetic acid (DTPA also known as pentaacetic acid) and the like). The compositions of the invention can also be at about pH 6.5–9.5.

In another embodiment, the composition contains 0–300 mM of one or more salts, for example chloride salts, 0–100 mM of one or more non-reducing sugars, 0–100 mM of one or more buffers, 0.01–0.5% of one or more surfactants, and 0–150 $\mu$M of one or more chelating agents. In a still further embodiment, the composition contains 0–150 mM NaCl, 0–10 mM sodium phosphate, and 0.01–0.1% surfactant, and 0–50 $\mu$M of one or more chelating agents, pH 6.6–7.8. Most preferably, the hemoglobin-containing composition includes 5 mM sodium phosphate, 150 mM NaCl, 0.025% to 0.08% polysorbate 80, and 25 $\mu$M EDTA, pH 6.8–7.6.

Additional additives to the formulation can include antibacterial agents, oncotic pressure agents (e.g. albumin or polyethylene glycols) and other formulation acceptable salts, sugars and excipients known in the art. Each formulation according to the present invention can additionally comprise constituents including carriers, diluents, fillers, salts, and other materials well-known in the art, the selection of which depends upon the particular purpose to be achieved and the properties of such additives which can be readily determined by one skilled in the art.

The compositions of the present invention can be formulated by any method known in the art. Such formulation methods include, for example, simple mixing, sequential addition, emulsification, diafiltration and the like.

Pharmaceutical compositions of the invention can be useful for, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection. Non-pharmaceutical compositions of the invention can be used as, for example, reference standards for analytical instrumentation needing such reference standards, reagent solutions, control of gas content of cell cultures, for example by in vitro delivery of oxygen to a cell culture, and removal of oxygen from solutions.

In one embodiment, the compositions can be formulated for use in therapeutic applications. For example, the formulations of the present invention can be used in compositions useful as substitutes for red blood cells in any application that red blood cells are used. Such compositions of the instant invention formulated as red blood cell substitutes can be used for the treatment of hemorrhage where blood volume is lost and both fluid volume and oxygen carrying capacity must be replaced. Moreover, because the compositions of the instant invention can be made pharmaceutically acceptable, the formulations of the instant invention can be used not only as blood substitutes that deliver oxygen but also as simple volume expanders that provide oncotic pressure due to the presence of the large hemoglobin protein molecule.

A typical dose of hemoglobin as a blood substitute is from 10 mg to 5 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, the particular purpose to be achieved according to the determination of the ordinarily skilled artisan in the field.

Administration of extracellular hemoglobin can occur for a period of seconds to hours depending on the purpose of the hemoglobin usage. For example, as a blood delivery vehicle, the usual time course of administration is as rapid as possible. Typical infusion rates for hemoglobin solutions as blood replacements can be from about 100 ml to 3000 ml/hour. However, when used to stimulate hematopoiesis, administration can last only seconds to five minutes and therefore administration rates can be slower because the dosage of hemoglobin is much smaller than dosages that can be required to treat hemorrhage.

In a further embodiment, the formulation of the instant invention can be used to treat anemia, both by providing additional oxygen carrying capacity in a patient that is suffering from anemia, and by stimulating hematopoiesis. In addition, because the distribution of the hemoglobin in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation and the like.

The compositions of the instant invention can also be used as replacement for blood that is removed during surgical procedures where the patient's blood is removed and saved for reinfusion at the end of surgery or during recovery (acute normovolemic hemodilution or hemoaugmentation).

Because the hemoglobin of the instant invention can bind nitric oxide and other non-oxygen ligands as well as oxygen, the formulations of the instant invention are also useful for the binding or delivery of nitric oxide or non-oxygen ligands. These non-oxygen ligands can be bound or delivered both in vivo or in vitro. For example, the hemoglobin of the instant invention may be used to remove excess nitric oxide from a living system. Excess nitric oxide has been implicated in conditions ranging from hypotension to septic shock. Likewise, nitric oxide or other non-oxygen ligands may be delivered to a system to alleviate a disease condition. For example, nitric oxide could be delivered to the vasculature to treat hypertension. Other therapeutic uses of the instant invention can include drug delivery and in vivo imaging.

The composition of the present invention can also be used for a number of in vitro applications. For example, the delivery of oxygen by the composition of the instant invention can be used for the enhancement of cell growth in cell culture by maintaining oxygen levels in vitro. Moreover, the hemoglobin of the instant invention can be used to remove oxygen from solutions requiring the removal of oxygen, and as reference standards for analytical assays and instrumentation.

The compositions of the instant invention can be stored at temperatures less than 40° C. for periods of 12 months or more. Preferably, the hemoglobin of the present invention can be stored at 25° C. for periods of 12 months or more. More preferably the solution can be stored at 25° C. for periods of at least 6 months, most preferably the solution of the instant invention can be stored at 25° C. for at least three months. In another embodiment, the solutions of the instant invention can be stored at 4° C. for at least 6 months, more preferably 12 months. In a further embodiment, the solutions of the instant invention can be stored at temperatures less than 4° C. for at least three months.

The hemoglobin solutions of the instant invention can be stored in oxygen impermeable containers, for example, stainless steel tanks, oxygen impermeable plastic bags, or plastic bags overwrapped with low oxygen permeably plastic bags wherein an oxygen scavenger is placed between the internal plastic bag and the overwrapped plastic bag. In another embodiment, the storage stable hemoglobin solutions can be stored in oxygen permeable or oxygen impermeable containers in an oxygen controlled environment. Such oxygen controlled environments can include, for example, glove boxes, glove bags, incubators and the like. Preferably the oxygen content of the oxygen controlled environment is low relative to atmospheric oxygen concentrations.

Stability of the hemoglobin solutions of the instant invention can be determined by any means accepted in the art.

Generally, stability can be determined by the measurement of degradation of the hemoglobin, such as the formation of oxidation, proteolytic or deamidation products, changes in molecular weight distribution, changes in potency, changes in functionality, increases in insoluble matter such as aggregates or modification of the product due to the presence of excipients, such as non-enzymatic glycation. In addition, stability can be determined as a loss of sterility or changes in concentration due to for example, volatilization, adsorption, chemical modification and the like. Preferably, stability of hemoglobin solutions is determined by measurement of functionality, measurement of oxidation products, changes in molecular weight distribution and increases in degradation products. Such degradation can be monitored by changes in the ratio of beta globin to alpha globin as described, for example, in Example 1. Accordingly, storage stable hemoglobin solutions are those solutions of hemoglobin that show less than 10% hemoglobin degradation, less than 10% change in molecular weight distribution, or contain less than 5% methemoglobin. Storage stable solutions can also show any combination of these characteristics. The hemoglobin comprising the storage stable solution can have the functionality necessary for a specific application. For example, if the storage stable hemoglobin of the present invention is to be used as a blood substitute, then it should have a $P_{50}$ greater than about 27 mm Hg, or have an $n_{max}$ greater than about 1.7.

EXAMPLES

The following examples are provided by way of describing specific embodiments of the present invention without intending to limit the scope of the invention in any way.

Example 1

Stability Measurement Techniques

Measurement of molecular weight distribution

The molecular weight distribution of the hemoglobin composition of the instant invention was determined as follows. Hemoglobin solutions were diluted to approximately 4 mg/ml concentrations in 5 mM sodium phosphate, 150 mM NaCl, pH 7.6. Aliquots (25 μl) were chromatographically separated using a Pharmacia "SUPEROSE" 12 (Piscataway, N.J.) size exclusion column. The columns were eluted with the same buffer as the dilution buffer at a flow rate of 0.5 ml/min. Absorbance was monitored at 280 nm.

Measurement of globin composition

The degradation of the hemoglobin molecule can be determined by monitoring modification of the beta globin. A simple method for the quantitation of beta globin modification is by determination of changes in relative globin composition (i.e. beta globin content versus alpha or di-alpha globin content). Either the alpha globin peak area or the di-alpha globin peak can be used in the analysis. Use of the appropriate peak will depend on the composition of the hemoglobin under examination.

The globin composition (beta globin and di-alpha globin) of the hemoglobin was determined as follows. Heme was removed from hemoglobin solutions by precipitating with a cold acid acetone solution (0.6% HCl/acetone). Hemoglobin was diluted to approximately 10 μg/μl with HPLC grade water. 100 μl of this diluted hemoglobin solution was mixed with the cold acid-acetone mixture, allowed to precipitate and microcentrifuged to separate the fractions. The supernatant was aspirated and discarded; the pellet was dried with a stream of argon and stored at −20° C. until chromatographic analysis.

HPLC was performed using a Zorbax C3 HPLC analytical column (MAC-MOD Analytical, Inc., Chadds Ford, Pa.). Prior to analysis, the pellet was resuspended in 0.5 ml of 0.1% trifluoroacetic acid (TFA) to yield a final concentration of approximately 2 mg/ml. Any residual undissolved material was removed by spinning the sample for 10 minutes in a microcentrifuge prior to application on the analytical column. Approximately 100 μg of protein were separated on the Zorbax column using the following separation regime: 35% solvent B for five minutes, then linear ramp to 49% solvent B during the next 45 minutes, where solvent A was 0.1% TFA in HPLC-grade water and solvent B was 0.1% TFA in acetonitrile. The flow rate for the separation was 1 ml/min. Absorbance was monitored at 215 nm.

The area of the beta polypeptide peak changed significantly under certain conditions. For example, the area of the beta peak for hemoglobin stored under high oxygen conditions in the presence of increasing ascorbate concentrations had decreased markedly during 21 days of storage. The decrease in the area of the beta peak resulted in a reduction of the ratio of the beta globin peak area to the di-alpha globin peak area. Because of minor differences in the initial di-alpha content of a given hemoglobin solution, the ratio of the area of the beta peak to the di-alpha peak provided a measure of the degradation of the hemoglobin solutions that could be used for comparison of the effectiveness of different storage conditions for different hemoglobin solutions. As shown in Table 1, solutions prepared according to Example 2 and analyzed for the beta/di-alpha peak ratio as described above appeared to be stable at beta/di-alpha ratios of greater than 0.9 if methemoglobin formation was controlled. A beta/di-alpha ratio of 0.9 is considered to be equivalent to approximately 10% degradation of hemoglobin.

$P_{50}$ and $n_{max}$ determination $P_{50}$ and $n_{max}$, functional properties of the hemoglobin, were determined by oxygen equilibrium binding experiments using a HEMOX instrument (TCS, Inc.) as described in Hoffman and Nagai, U.S. Pat. No. 5,028,588, herein incorporated by reference. $P_{50}$ and $n_{max}$ were determined at 37° C., 50 mM HEPES, 100 mM Cl$^-$, pH 7.4.

Methemoglobin concentration

Methemoglobin is hemoglobin wherein one or more of the irons of the heme prosthetic groups are in the $Fe^{+3}$ (ferric) oxidation state. The measurement technique for methemoglobin described herein measures the oxidation state of individual heme irons. Thus, the reported percentage of methemoglobin reflects the percentage of hemes that are oxidized in the hemoglobin sample.

Five microliters of hemoglobin solutions were added to 500 μl of 0.1 M Tris, pH 8.0. 200 μl of the diluted hemoglobin solution was then added to 2.8 ml of 0.1 M Tris, pH 8.0 in a 4.5 ml cuvette for a final dilution of 1:1500. The oxygenated sample (Hb) was then analyzed by spectrophotometry in a Hewlett-Packard model HP 8452A spectrophotometer. Absorbances at 436, 425, 420, 404, 400 nm were collected and stored in a data storage system. The cuvette was then removed from the spectrophotometer and sparged with carbon monoxide two times for 15 seconds each time. The cuvette was inverted 5 times between each sparge. The sample was then re-inserted into the spectrophotometer, and a second set of spectra were collected that corresponded to carbonmonoxy hemoglobin (HbCO). The cuvette was then again removed from the spectrophotometer and 30 μl of 0.1 M KCN in 0.1 M Tris, pH 8.0 was added to the sample. The sample was then inverted three times, allowed to incubate for 5 minutes, and re-inserted into the spectrophotometer for a final spectrophotometric analysis (HbCN). The percent methemoglobin was then calculated as follows:

$$\% \text{Met Hb} = \frac{[A_{425}^{HbCN} - A_{404}^{HbCN}] - [A_{425}^{Hb} - A_{404}^{Hb}]}{[A_{420}^{HbCO} - A_{436}^{HbCO}] - [A_{420}^{Hb} - A_{436}^{Hb}] + [A_{425}^{HbCN} - A_{404}^{HbCN}] - [A_{425}^{Hb} - A_{404}^{Hb}]} * 100$$

where A=the absorbance at the susbcripted wavelength for the superscripted hemoglobin species.

Example 2

Preparation of Hemoglobin Solutions for Stability Studies

Hemoglobin was expressed, prepared and purified as described in co-owned PCT patent application number, PCT/US94/13034, filed Nov. 14, 1994, entitled "Purification of Hemoglobin", incorporated herein by reference. The hemoglobin was then concentrated by diafiltration to a concentration of 100 mg/ml and polysorbate 80 was added to a final concentration of 0.03% (w/v). The hemoglobin solution was then deoxygenated by flowing oxygen-free nitrogen gas over the hemoglobin solution for approximately 2 hours in a round bottomed flask. The solution was deoxygenated with nitrogen and then equilibrated with the oxygen mixture chosen for the study.

Ascorbate was prepared as a 0.5 M stock solution. The ascorbate solution was then deoxygenated by repeated evacuations of the stock solution and flushing with oxygen-free nitrogen gas four to five cycles. The ascorbate solutions were made up freshly for each experiment described herein. Once the ascorbate solution was prepared, it was moved into a glove bag (the "fill environment") along with the deoxygenated hemoglobin solution and the glove bag was equilibrated to the required residual level of oxygen in the headspace of the globe bag by repeated evacuations and flushing with the appropriate oxygen/nitrogen mixture. The residual oxygen concentration in the glove bag was determined using a "MOCON" apparatus as described above. After equilibration of the glove bag, the ascorbate and the hemoglobin solution were opened, and ascorbate was added to final concentrations of 0.5 to 5 mM. The hemoglobin solutions containing ascorbate were aliquoted into 2 ml glass vials as 0.5 ml aliquots. The vials were capped with gray butyl rubber stoppers and crimp sealed. The solutions were removed from the glove bag and stored in temperature controlled incubators at either 4° C. or 25° C. under ambient gas conditions.

Solutions were stored for up to three months. Vials were withdrawn from the stored samples at appropriate time points for given stability test. These tests included, reverse phase HPLC analysis for the determination of the beta and di-alpha content, molecular weight distribution by high performance size exclusion chromatography (HP-SEC), functionality determinations using $P_{50}$ and $n_{max}$ values, and methemoglobin concentration.

Example 3

Oxygen/Ascorbate Titration Studies: effect on beta/di-alpha ratio and methemoglobin concentration To determine the effect of ascorbate concentration on the stability of hemoglobin over time, solutions of hemoglobin were prepared as described above. These solutions contained 150, 1000, 5000 and 15000 ppm oxygen in the headspace and either 0.5, 1, 2 and 5 mM concentrations of ascorbate in the solution (ratios of 0.3:1, 0.6:1, 1.3:1 and 3.2:1 ascorbate to hemoglobin molar ratios respectively). Solutions were stored for 3 weeks at 4° C. The beta to di-alpha ratio and the percentage of methemoglobin in the solutions was determined at the end of the storage period. The greatest change in the beta/di-alpha ratio was observed in samples containing high levels of both ascorbate and residual oxygen, while the greatest increase in percentage methemoglobin was observed in formulations containing oxygen and low ascorbate (Table 1). At low residual oxygen levels (1000 ppm and lower) there was little change in the beta/di-alpha ratio whether or not there was ascorbate in the formulation. However, if there was no ascorbate in the formulation, there were high levels of methemoglobin in the formulation at the end of the storage period. At high residual oxygen levels (5000 and 15000 ppm), the high ascorbate formulations (ascorbate greater than approximately 0.5 mM) showed greater changes in the beta/di-alpha ratio (see FIG. 2 and Table 1) than the low ascorbate formulations. In addition, there was appreciable formation of methemoglobin in high residual oxygen formulations. It is of note that at the end of the storage period, methemoglobin was maintained at low levels except in the presence of greater than 5000 ppm oxygen and less than 1 mM ascorbate. Thus even when there was no appreciable formation of methemoglobin in the hemoglobin formulation, there was modification of the polypeptide subunits.

TABLE 1

Beta/di-alpha ratios and % methemoglobin in hemoglobin solutions stored for 21 days at 4° C.

| | 150 ppm $O_2$ | | 15000 ppm $O_2$ | |
| --- | --- | --- | --- | --- |
| | beta/di-alpha | % methemoglobin | beta/di-alpha | % methemoglobin |
| 0 mM ascorbate | 1.00 | 19.18 | 0.97 | 39.82 |
| 0.5 mM ascorbate | 0.99 | 1.48 | 0.88 | 46.21 |
| 1 mM ascorbate | 1.00 | 1.00 | 0.82 | 45.06 |
| 2 mM ascorbate | 0.98 | 0.7 | 0.78 | 3.34 |
| 5 mM ascorbate | 0.99 | 0.54 | 0.72 | 1.50 |

Example 4

Oxygen/Ascorbate Titration Studies: effect on functionality

To determine the effect of ascorbate concentration on the functionality of hemoglobin over time, solutions of hemoglobin were prepared as described above in Example 4. The functionality of the hemoglobin in the solution was determined at the end of the three week storage period by the determination of $P_{50}$ and $n_{max}$ as described above. There were minimal differences in the $P_{50}$ and $n_{max}$ values at the 150 and 1000 ppm residual oxygen levels for the different ascorbate concentrations (Table 2). However, at 5000 and 15000 ppm residual oxygen concentrations, higher ascorbate concentrations were accompanied by increases in $P_{50}$ values. Furthermore, at 15000 ppm residual oxygen concentration, the $n_{max}$ decreased with increasing ascorbate concentration (Table 2).

TABLE 2

| Ascorbate (mM) | Headspace Oxygen Concentration | | | | | | | |
|---|---|---|---|---|---|---|---|---|
| | 150 ppm | | 1000 ppm | | 5000 ppm | | 15000 ppm | |
| | $P_{50}$ | $n_{max}$ | $P_{50}$ | $n_{max}$ | $P_{50}$ | $n_{max}$ | $P_{50}$ | $n_{max}$ |
| 0 | 33.4 | 2.14 | 32.2 | 2.07 | 32.2 | 1.87 | 28.5 | 1.7 |
| 0.5 | — | — | 34.7 | 2.16 | 33.0 | 1.79 | — | — |
| 1 | 33.5 | 2.18 | 34.0 | 2.16 | 34.8 | 1.89 | 33.0 | 1.51 |
| 2 | — | — | 34.6 | 2.16 | 35.0 | 1.92 | — | — |
| 5 | 33.8 | 2.11 | 33.7 | 2.22 | 35.4 | 1.86 | 37.3 | 1.49 |

Example 5

Long term, room temperature storage of partially deoxygenated/ascorbate containing hemoglobin formulations Four different deoxygenated formulations, all containing 100 mg/ml hemoglobin and 2mM ascorbate and prepared as described in Example 2, were stored for 3 months at 25° C. The formulations all contained 150 mM NaCl, 5 mM sodium phosphate, 2 mM ascorbate, 0.03% polysorbate 80(standard formulation) and differed in the following manners:

(1) standard formulation, pH 6.75

(2) standard formulation, pH 7.21

(3) standard formulation, 25 μM EDTA, pH 6.75

(4) standard formulation, 25 μM EDTA, pH 7.21

Throughout the storage period, and at the completion of the 3 month storage period, samples were analyzed for methemoglobin content, changes in molecular weight measured as % high molecular weight hemoglobin (HMWHb), beta/di-alpha ratio, aggregate formation by both dynamic light scattering and light obscuration techniques and functionality ($P_{50}$ and $n_{max}$). At the conclusion of the storage period there had been no clinically relevant change in any of the parameters monitored throughout the study period (Table 3).

TABLE 3

| | Formulation #1 | | Formulation #2 | | Formulation #3 | | Formulation #4 | |
|---|---|---|---|---|---|---|---|---|
| | Initial | 3 months | Initial | 3 months | Initial | 3 months | Initial | 3 months |
| % metHb | 4.66 | 1.24 | 3.43 | 1.03 | 3.37 | 1.41 | 1.57 | 0.811 |
| % HMWHb | 1.67 | 2.16 | 1.81 | 2.42 | 1.67 | 2.4 | 1.73 | 2.53 |
| β/di-α | 1.05 | 0.941 | 0.99 | 0.962 | 1.05 | 0.954 | 1.02 | 0.966 |
| DLS (nm) | 6.4 | 7.1 | 6.5 | 9.75 | 6.2 | 8 | 6.5 | 6.2 |
| $P_{50}$ | 30.99 | 33.62 | 31.05 | 34.41 | 32.02 | 34.93 | 34.88 | 35.08 |
| $n_{max}$ | 2.23 | 2.02 | 2.19 | 1.94 | 2.17 | 1.98 | 2.35 | 1.94 |

The foregoing description of the invention is exemplary for purposes of illustration and explanation. It will be apparent to those skilled in the art that changes and modifications will be possible without departing from the spirit and scope of the invention. It is intended that the following claims be interpreted to embrace all such changes and modifications.

What is claimed is:

1. A storage stable hemoglobin composition comprising a partially deoxygenated hemoglobin solution and less than 4 moles of reducing agent per mole of hemoglobin to form said storage stable hemoglobin composition.

2. The composition of claim 1 wherein the partially deoxygenated hemoglobin solution contains less than 1000 parts per million of oxygen.

3. The composition of claim 2 wherein the partially deoxygenated hemoglobin solution contains less than 500 parts per million of oxygen.

4. The composition of claim 3 wherein the partially deoxygenated hemoglobin solution contains less than 150 parts per million of oxygen.

5. The composition of claim 1 wherein the reducing agent is selected from the group consisting of dithionite, sodium borohydride, and ascorbate.

6. The composition of claim 5 wherein the reducing agent is ascorbate.

7. The composition of claim 1 wherein the reducing agent is less than 3 moles of reducing agent per mole of hemoglobin.

8. The composition of claim 7 wherein the reducing agent is less than 2 moles of reducing agent per mole of hemoglobin.

9. The composition of claim 1 wherein the storage stable hemoglobin is storage stable for at least one year.

10. The composition of claim 1 wherein the storage stable hemoglobin is storage stable for at least six months.

11. The composition of claim 1 wherein the storage stable hemoglobin is storage stable for at least three months.

12. The composition of claim 1 wherein the storage stable hemoglobin is storage stable up to 40° C.

13. The composition of claim 12 wherein the storage stable hemoglobin is storage stable at about 25° C.

14. The composition of claim 11 wherein the storage stable hemoglobin is storage stable at about 4° C.

15. The composition of claim 12 wherein the reducing agent is ascorbate and the partially deoxygenated hemoglobin solution contains less than about 150 ppm oxygen.

16. A method of making a storage stable hemoglobin composition comprising combining a partially deoxygenated hemoglobin solution with less than 4 moles of a reducing agent per mole of hemoglobin.

17. The method of claim 16 further comprising partially deoxygenating a hemoglobin solution.

18. The method of claim 17 wherein the deoxygenation is by gas-liquid contacting methods.

19. The composition of claim 1 further comprising a pharmaceutically acceptable carrier.

20. The composition of claim 19 wherein said carrier contains at least one pharmaceutically acceptable excipient.

21. The composition of claim 1 further having pH between about 6.5 and about 9.5.

22. The composition of claim 18 having pH between about 6.6 and about 7.8.

23. The composition of claim 14 having pH between about 6.8 and about 7.6.

24. The composition of claim 1 further comprising a chelating agent.

25. The composition of claim 24 wherein the chelating agent is selected from the group consisting of EDTA and DTPA.

26. The composition of claim 25 wherein the chelating agent is EDTA.

27. A system for the storage of stable hemoglobin solutions comprising:

a partially deoxygenated hemoglobin solution containing less than 4 moles of a reducing agent per mole of hemoglobin; and a container for storage of said partially deoxygenated hemoglobin solution.

28. A storage stable hemoglobin composition comprising a partially deoxygenated hemoglobin solution and less than 4 moles of reducing agent per mole of hemoglobin to form said storage stable hemoglobin composition, wherein said hemoglobin composition is storage stable for a period of at least three months when stored at a temperature of about 4° C.

29. A storage stable hemoglobin composition comprising a partially deoxygenated hemoglobin solution and less than 4 moles of reducing agent per mole of hemoglobin to form said storage stable hemoglobin composition, wherein said partially deoxygenated hemoglobin solution contains less than 1000 parts per million of oxygen.

30. A storage stable hemoglobin composition comprising a partially deoxygenated hemoglobin solution and less than 4 moles of reducing agent per mole of hemoglobin to form said storage stable hemoglobin composition, wherein said partially deoxygenated hemoglobin solution contains less than 1000 parts per million of oxygen, and wherein said hemoglobin composition is storage stable for a period of at least three months when stored at a temperature of about 4° C.

* * * * *

UNITED STATES PATENT AND TRADEMARK OFFICE
CERTIFICATE OF CORRECTION

PATENT NO : 5,929,031
DATED : July 27, 1999
INVENTOR(S): Bruce A. Kerwin et al.

It is certified that error appears in the above-identified patent and that said Letters Patent are hereby corrected as shown below:

Column 16, claim 13, line 28, "12" should read ---1---.

Column 16, claim 14, line 30, "11" should read ---1---.

Column 16, claim 22, line 62, "18" should read ---1---.

Column 16, claim 23, line 64, "14" should read ---1---.

Signed and Sealed this

Twenty-fifth Day of July, 2000

Attest:

Q. TODD DICKINSON

*Attesting Officer*           *Director of Patents and Trademarks*